United States Patent
Sharonov et al.

(10) Patent No.: US 8,971,989 B2
(45) Date of Patent: Mar. 3, 2015

(54) MAGNETIC FIELD DEVICE FOR MAPPING AND NAVIGATION IN LAPAROSCOPIC SURGERY

(71) Applicant: Covidien LP, Mansfield, MA (US)

(72) Inventors: Alexey Sharonov, Bethany, CT (US); Ravi Durvasula, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 4 days.

(21) Appl. No.: 13/717,741

(22) Filed: Dec. 18, 2012

(65) Prior Publication Data

US 2013/0190598 A1    Jul. 25, 2013

Related U.S. Application Data

(60) Provisional application No. 61/589,880, filed on Jan. 24, 2012.

(51) Int. Cl.
*A61B 5/05* (2006.01)
*A61B 19/00* (2006.01)

(52) U.S. Cl.
CPC ............... *A61B 5/05* (2013.01); *A61B 19/5244* (2013.01)
USPC ........... 600/410; 600/407; 600/409; 600/424; 600/425

(58) Field of Classification Search
None
See application file for complete search history.

(56) References Cited

U.S. PATENT DOCUMENTS

| | | |
|---|---|---|
| 4,416,289 A | 11/1983 | Bresler |
| 4,431,005 A | 2/1984 | McCormick |
| 5,099,845 A | 3/1992 | Besz et al. |
| 5,425,382 A | 6/1995 | Golden et al. |
| 5,443,077 A | 8/1995 | Krogh et al. |
| 5,456,718 A | 10/1995 | Szymaitis |
| 5,494,035 A | 2/1996 | Leuthold et al. |
| 5,694,952 A | 12/1997 | Lidman et al. |
| 5,772,593 A | 6/1998 | Hakamata |
| 6,173,715 B1 | 1/2001 | Sinanan et al. |
| 6,216,028 B1 | 4/2001 | Haynor et al. |
| 6,263,230 B1 | 7/2001 | Haynor et al. |
| 6,297,736 B1 | 10/2001 | Lewis et al. |
| 6,381,485 B1 | 4/2002 | Hunter et al. |
| 6,402,762 B2 | 6/2002 | Hunter et al. |
| 6,418,335 B2 | 7/2002 | Avrin et al. |
| 6,427,314 B1 | 8/2002 | Acker |
| 6,496,713 B2 | 12/2002 | Avrin et al. |
| 7,561,051 B1 | 7/2009 | Kynor et al. |
| 7,696,876 B2 | 4/2010 | Dimmer et al. |
| 7,778,687 B2 | 8/2010 | Dimmer et al. |
| 8,011,508 B2 | 9/2011 | Seiler et al. |
| 2003/0125759 A1 | 7/2003 | Mirizzi et al. |

(Continued)

FOREIGN PATENT DOCUMENTS

| | | |
|---|---|---|
| WO | WO 2007/094002 A2 | 8/2007 |
| WO | WO 2010/026357 A1 | 3/2010 |

OTHER PUBLICATIONS

European Search Report for EP 12 18 0079 dated Dec. 4, 2012.

*Primary Examiner* — Joel Lamprecht

(57) ABSTRACT

Devices, systems and methods for using those devices and systems are disclosed to facilitate mapping and navigation during a minimally invasive surgical procedure. These devices, systems and methods include implantable magnetic devices and sensing devices that facilitate locating the implantable magnetic devices such that a surgeon can accurately locate and place devices at particular points of interest during a medical procedure.

14 Claims, 3 Drawing Sheets

(56) References Cited

U.S. PATENT DOCUMENTS

| | | |
|---|---|---|
| 2006/0224148 A1 | 10/2006 | Cho et al. |
| 2007/0010702 A1* | 1/2007 | Wang et al. .................. 600/8 |
| 2007/0055144 A1* | 3/2007 | Neustadter et al. ........... 600/425 |
| 2007/0167701 A1 | 7/2007 | Sherman |
| 2008/0139915 A1 | 6/2008 | Dolan et al. |
| 2009/0198293 A1 | 8/2009 | Cauller et al. |
| 2010/0094116 A1 | 4/2010 | Silverstein |
| 2010/0275934 A1 | 11/2010 | Keren |
| 2011/0264104 A1 | 10/2011 | Naoum |

* cited by examiner

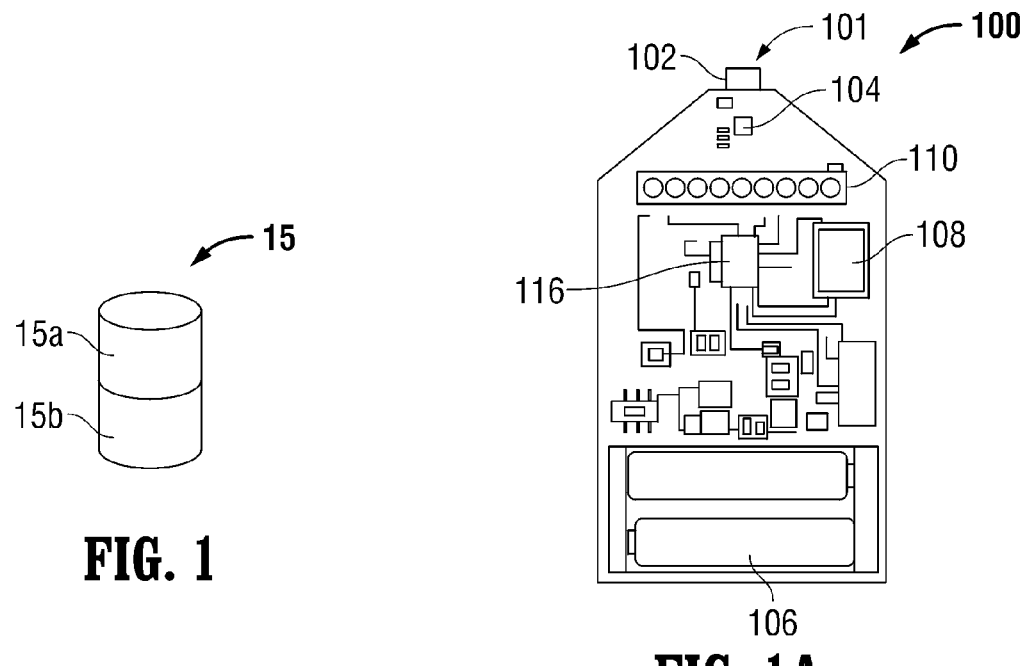
FIG. 1
FIG. 1A
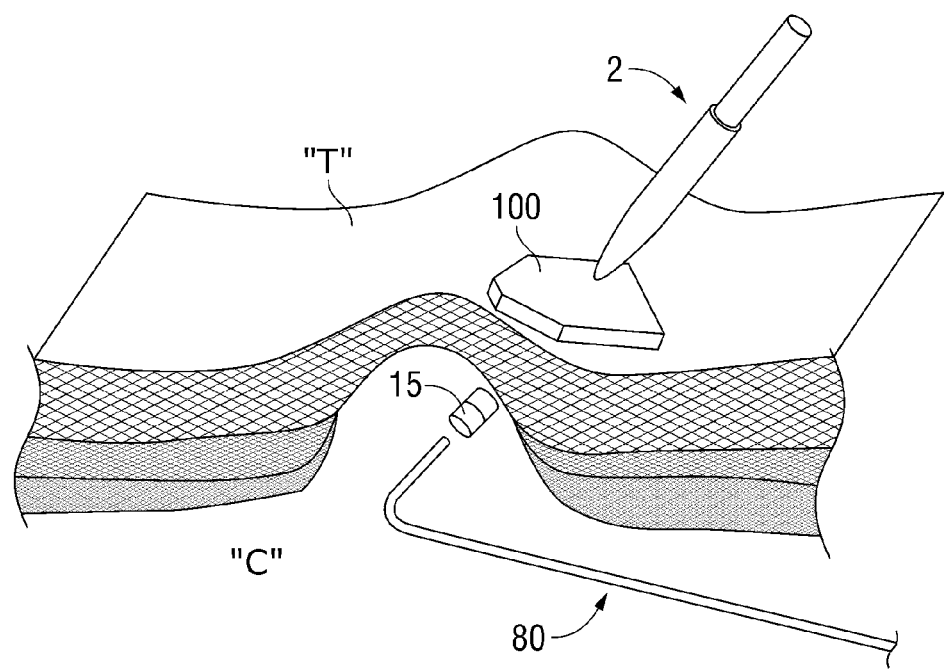
FIG. 2

MAGNETIC FIELD DEVICE FOR MAPPING AND NAVIGATION IN LAPAROSCOPIC SURGERY

CROSS REFERENCE TO RELATED APPLICATION

The present application claims the benefit of and priority to U.S. Provisional Application Ser. No. 61/589,880, filed on Jan. 24, 2012, the entire contents of which are incorporated herein by reference.

BACKGROUND

1. Technical Field

The present disclosure relates generally to devices, systems, and methods for marking and locating points of interest during a surgical procedure, and more particularly to a magnetic field device for mapping and navigating during a minimally invasive surgical procedure.

2. Background of Related Art

Many surgical procedures necessitate determining the location of surgical tools or internal features within a patient's body. Often these devices and/or internal features are not readily locatable without costly and time consuming procedures. Various imaging devices, e.g., MRI and/or x-ray, may be used to view the inside of a patient's body.

However, such devices may not be suitable during a surgical procedure where the location of such structures may have to be determined rapidly. In addition, imaging devices that utilize radiation may be detrimental to the health of a patient. Moreover, the images taken by the imaging devices, e.g., MRI and/or x-ray, may have to be developed and analyzed by specialized technicians. In addition, such procedures are often costly. Often, once particular areas are identified, a surgeon will place a physical marker in that location, e.g., form an incision and place a cannula at that location. It would be desirable to have less damaging ways to mark and label areas of interest in real-time.

Consequently, a continuing need exists for devices and methods that can accurately and rapidly locate instruments and structures within a patient's body during the course of a surgical procedure.

SUMMARY

The present disclosure relates to systems, devices, and methods for use in a minimally invasive surgical procedure to map the position of underlying structures, e.g., body structures or surgical devices and/or instruments.

A surgical mapping system for locating structures under body tissue may include one or more magnets, e.g., permanent magnets, that are configured to be emplaced under tissue within a body cavity. The methods may be emplaced with a grasper or temporarily affixed affixed to an implant, such as a hernia mesh, or affixed to tissue using fastening methods such as a suture, barbs, staples or other fasteners. Each magnet produces a magnetic field having a magnitude that is greater closer to the magnet than it is at farther distances from the magnet. A mapping device includes one or more sensors, each configured to detect the magnitude of the magnetic field and an indicator providing an indication of the magnitude of the magnetic field at a location. By sensing the magnitude of the magnetic field, the placement of the magnets under the tissue may be determined through trial and error by moving the mapping device until receipt of an appropriate indication by the indicator that the mapping device is aligned with the emplaced magnet.

The indicator may include one or more light sources, e.g., light emitting diodes (LEDs), that may increase in brightness as the mapping source gets closer to the emplaced magnets. The one or more light sources may also include a number of light sources and may be arranged in a row to provide a light indicator bar. As the mapping device is positioned closer to an magnet, a greater number of the light sources may become illuminated.

Once underlying magnets are located, their locations may be marked electronically on monitoring systems or physically on the patient's skin. For example, a marker may be used to mark the locations on the skin at the locations where the magnets are underneath. The mapping device may include an aperture for the reception of the marker to facilitate marking the skin.

During use, points of interest or locations under the tissue and/or within the body cavity are marked by implanting magnets at those locations. The marked locations are readily found using the above described mapping devices. During use, the operator of the mapping device will move the mapping device along the surface of a patient's tissue, e.g., the patient's tissue, and will observe indications from the indicator as to the strength of the magnetic fields in the locations where the mapping device is moved. By trial and error, each of the magnets will be located by finding those locations where the magnetic field is strongest.

These and other embodiments of the present disclosure will be described in greater detail hereinbelow.

BRIEF DESCRIPTION OF THE DRAWINGS

Embodiments of the present disclosure are described herein with reference to the accompanying drawings, wherein:

FIG. 1 is a perspective view of a magnet;

FIG. 1A is a top view of a mapping device in accordance with the present disclosure;

FIG. 2 illustrates locating and marking the location of the emplaced magnet of FIG. 1 by using the mapping device of FIG. 1A;

DETAILED DESCRIPTION

Figure 3:
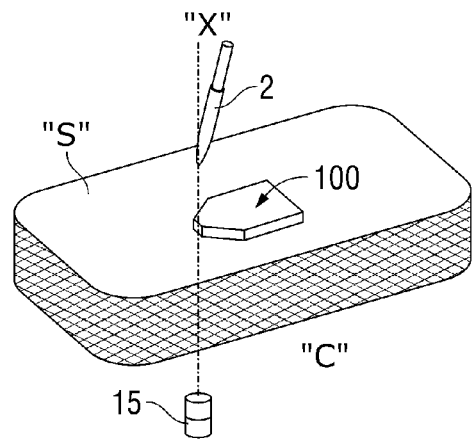
FIG. 3 illustrates the mapping device of FIG. 1A placed on a tissue surface and aligned along a common axis with the magnet of FIG. 1 and a marking device.

Particular embodiments of the present disclosure will be described herein with reference to the accompanying drawings. In the figures and in the description that follows, in which like reference numerals identify similar or identical elements, the term "proximal" will refer to the end of the apparatus that is closest to the operator during use, while the term "distal" will refer to the end that is farthest from the operator during use.

Devices, systems, and methods for mapping the locations of internal bodily structures are described in detail below. The placement or implantation of magnets, e.g., permanent magnets, at desired locations within the surgical site facilitates later location of these locations. Mapping internal structures is desirable in many procedures including hernial repairs (e.g., inguinal, ventral, and umbilical hernial repairs). During a hernial repair, a mesh, e.g., a woven material, is often emplaced to patch an area of weakness or to plug holes. The mesh is placed either under or over the defect in the abdominal wall and held in place by sutures. In essence, the mesh functions as "scaffolding" for new growth of a patient's own tissue, which eventually incorporates the mesh into the surrounding area.

A hernial mesh may fail because of inadequate overlap of the mesh covering the hernia defect or inaccurate placement of sutures holding the mesh in place. Such failures may be inhibited by facilitating accurate and precise placement of the mesh at the areas of defect. It is with this in mind that the devices, systems, and methods will be described with reference to the repair of a hernial defect. Currently, a surgeon may create a map for himself by locating defects, creating a hole in the defect, and placing a cannula through the defect. The devices, systems, and methods described in detail below minimize the need to create holes through the defect itself by providing another way to mark and map these locations.

It is to be understood that hernial repair is only an exemplary use, and that the devices, systems, and methods disclosed herein may be utilized during any surgical procedure where it is desirable to guide a surgeon to internal structures and/or facilitate the creation of a map that will help precisely guide the surgeon to targeted locations within the surgical site.

An implantable magnet 15 (FIG. 1) may be placed underneath a tissue surface "T", e.g., abdominal wall (FIGS. 2 and 3B) within a body cavity "C", e.g., abdominal cavity. As shown in FIG. 1, the magnet 15 may be a permanent magnet including a first pole 15a and a second pole 15b that are commonly referred to as "north" and "south" poles. Although magnet 15 may be substituted by other devices that emit a magnetic field, a permanent magnet such as magnet 15 is relatively inexpensive, requires no batteries, and requires little or no maintenance. The magnet 15 emits a magnetic field that can be measured in the international unit of magnetic flux density called "Tesla" ("T"). The magnetic field, $B_{axis}$ (measured in tesla) of an ideal dipole measured along its axis is calculated as follows: $B_{axis}=[(\mu_0)/(4\pi)] \times [(2\mu)/d^3]$, where $\mu_0$ is the permeability constant ($4\pi \times 10^{-7}$ T m/A), d is the distance from the center of the dipole in meters, and $\mu$ is the magnetic moment. The magnetic moment $\mu$ measures the strength of the magnet. As seen from this equation, the strength of the magnetic field is distance dependant. The magnetic field strength will weaken rapidly when moved a short distance away from the magnet, and will change relatively slowly at distances farther away from the magnet.

As shown in FIG. 2, magnet 15 is emplaced on the underside of tissue "S". During a hernial repair, for example, the location where the magnet 15 is placed may be an area that has been identified as having a defect. An instrument 80 that is configured and adapted for use during a minimally invasive surgical procedure and including an end effector that is capable of grasping the magnet 15 may be used to implant the magnet 15 at a desired location, e.g., a hernial defect. Once the magnet 15 is emplaced it may serve as a beacon by sending signals, i.e., emitting a magnetic field, to a suitable device that can detect and locate the magnet 15, thereby facilitating the relatively rapid relocation of the point of interest.

Mapping devices 100, 200 (FIGS. 1A and 4) that are configured to detect the magnet 15 and guide a surgeon to its location are described hereinbelow. As shown in FIG. 1A, a mapping device 100 includes a magnetic field sensor 102, a first indicator 104 and/or a second indicator 110, a threshold button 108, and a power source 106. The mapping device 100 is configured and adapted to locate implants that emit a magnetic field by detecting the strength of the magnetic field emitted by the implant, e.g., a magnet. The mapping device 100 is configured and adapted to provide indication to a user when the mapping device 100 is being moved toward or away from the implant.

The magnetic field sensor 102 measures the magnetic field strength. Suitable magnetic field sensors 102 include, but are not limited to, Hall sensors and/or magnetoresistive sensors. The first indicator 104 may be a single light, e.g., a light emitting diode (LED). The second indicator 110 may be a light bar including a plurality of lights, e.g., an array of LEDs. As the magnetic field strength changes as the distance between the field sensor 102 and the magnet 15 changes, the brightness of the LEDs may change, e.g., brighter when in close proximity and dimmer when distant, and/or the number of LEDs illuminated may change, e.g., a stronger magnetic field corresponds to a greater number of illuminated LEDs and a weaker magnetic field corresponds to a lesser number of illuminated LEDs.

As discussed above, the magnetic field strength of a permanent magnet changes with respect to distance in an inverse cubed relation. This means that the magnetic field strength changes rapidly as the field sensor 102 and the magnet 15 approach one another. Therefore, it may be convenient to implement an autoscale feature. An exemplary processing algorithm will now be described. However, it is to be understood that other processing procedures may be used. For example, at power up, the field sensor 102 reads the magnetic field at a given location. The level of residual magnetic field, which varies by the environment, is determined by calculating an average. The difference of current field measurement and the initial level is represented by the first and/or second indicators 104, 110. As the brightness and/or bar length (number of illuminated lights) approaches the maximum level, the scale is automatically changed, e.g., to 20% of sensitivity, from the previous value. The sensitivity of the field sensor 102 may be auto-adjusted. For example, at the start of the procedure, the sensitivity is high enough to detect a small permanent magnet at distances such as 10 centimeters, and at the final stage, the magnet can be as close as 1 centimeter (field increases for several orders of magnitude) but still provide non-saturated indication because scale is automatically adjusted to a level when a stronger field can be detected. Also, as shown in FIG. 1A, the mapping device 100 may include a threshold button 108 which may be used to set the current field level at the zero level. After activating the threshold button 108, only magnetic fields having a greater value will be displayed. The threshold button 108 may also be used to reset the indicator scales of the first and/or second indicators 104, 110 back to their original level of sensitivity.

A processing unit 116 may execute the above described algorithm and control the provided indication. The processing unit 116 may include any type of computing device, computational circuit, or any type of process or processing circuit capable of executing a series of instructions that are stored in memory. The processing unit 116 may include multiple processors and/or multicore CPUs and may include any type of processor, such as a microprocessor, digital signal processor, microcontroller, or the like. A power source 106 may include an internal battery to power the mapping device 100.

During use, as shown in FIGS. 2 and 3, the mapping device 100 is moved along a surface of tissue "S", e.g., a patient's abdomen. Through trial and observation, the mapping device 100 is moved along the surface of the tissue "S" until the highest strength magnetic field is observed and indicated by the first and/or second indicators 104, 110, thereby notifying the user that the magnet 15 and the mapping device 100 are at closet proximity. A proximal end 101 of the mapping device 100 may be generally pointed to facilitate marking of the tissue "S" at a particular location.

Figure 4:
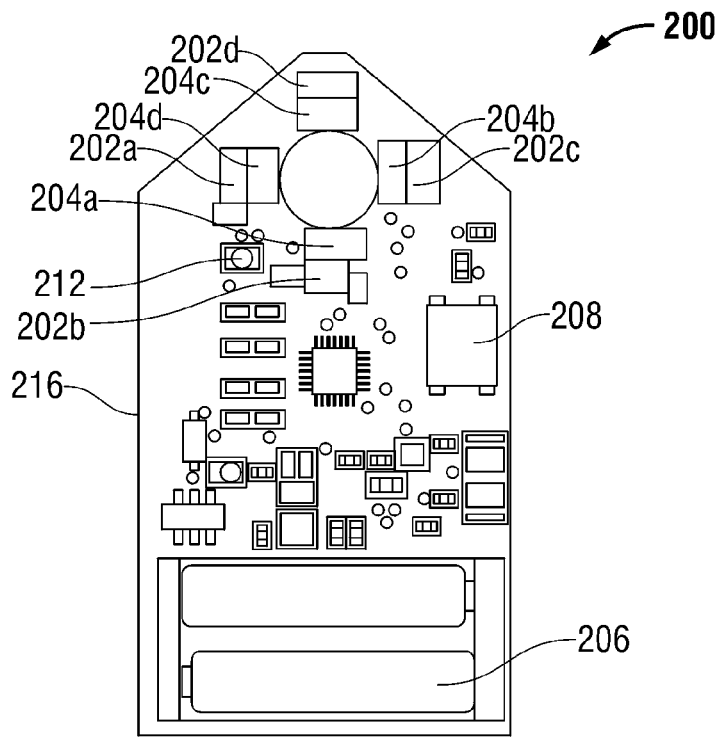
FIG. 4 is a top view of another mapping device in accordance with the present disclosure.
Figure 5:
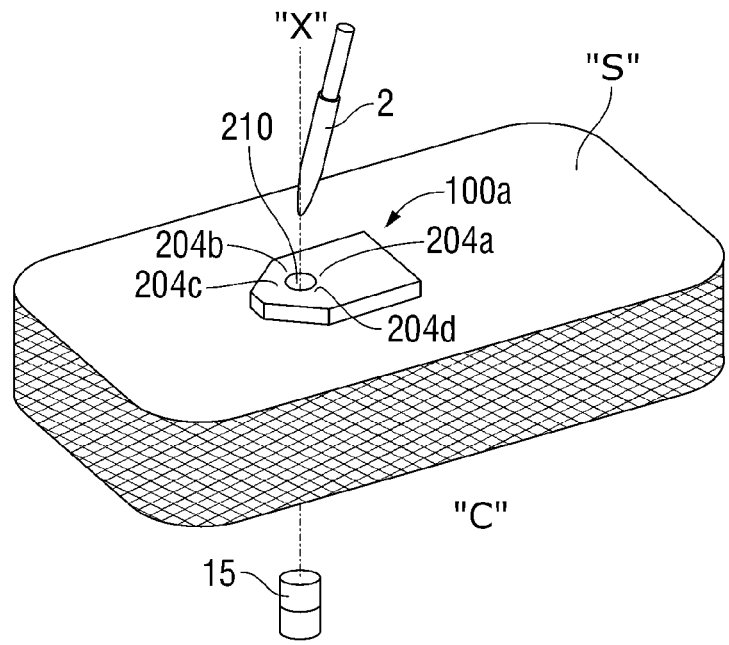
FIG. 5 illustrates the mapping device of FIG. 4 aligned with a marker, and the magnet of FIG. 1 on the underside of tissue.

In embodiments, a mapping device may include one or more sensors that can detect the magnetic field at more than one location or along more than one axis. The mapping device 200, as illustrated in FIG. 4, includes four sensors 202*a-d* that are evenly spaced at the same distance from the center of an aperture 210. A power source 206 may include an internal battery to power the mapping device 200. In addition, the algorithms employed in controlling when the various indications are provided are controlled by a processing unit 216 that may include any type of computing device, computational circuit, or any type of processor or processing circuit capable of executing a series of instructions that are stored in a memory. The processing unit 216 may include multiple processors and/or multicore CPUs and may include any type of processor, such as a microprocessor, digital processor, microcontroller, or the like.

The mapping device 200 may include a strength indicator 212, e.g., a light (e.g., LED) of variable intensity, and one or more directional indicators 204*a-d* to provide guidance as to the source of the magnetic field. For example, four directional indicators 204*a-d* can directional guidance to move the mapping device 200 in a particular direction along the tissue "S" to bring the mapping device 200 closer to the emplaced magnet 15. As shown in FIG. 4, a first directional indicator 204*c* may be illuminated to instruct a user to move the mapping device 200 in an upward direction; a second directional indicator 204*a* may be illuminated to instruct a user to move the mapping device 200 in a downward direction; a third directional indicator 204*d* may be illuminated to instruct a user to move the mapping device 200 in a leftward direction; and a fourth directional indicator 204*b* may be illuminated to instruct a user to move the mapping device 200 in a rightward direction. A user may be instructed to move in more than one of these directions at the same time. For example, the first and second directional indicators 204*c*, 204*b* may be illuminated at the same time to instruct the user to move the mapping device in both an upward and rightward direction. Once the magnet 15 is located within the boundaries of aperture 210, an indication is provided, e.g., all of the indicators 204*a-d*, 212 are illuminated. The aperture 210 defines a space that facilitates marking the surface of the tissue "S" by placing a mark within the aperture 210. For example, a permanent ink marker may be used to place marks on the surface of the tissue "S". As the start of the procedure (as with the threshold button 108 of the mapping device 100), environmental magnetic field disturbance is minimized by depressing threshold button 208 such that a baseline magnetic field detected will not cause an indication to be provided.

The direction to the magnet 15 can be calculated using differential sensor reading in two orthogonal axes, e.g., 2-dimensional Cartesian coordinates x ("horizontal") and y ("vertical"). 3-dimensional coordinates may be determined by also reading the magnetic strength along a third dimension, z, thereby also determining the depth of the location of magnet 15. As discussed above, four sensors 202*a-d* surround central aperture 210. Each sensor 202*a-d* provides reading of the magnetic field strength at its location such that direction to the magnet 15 can be calculated using differential sensor reading in two orthogonal axes. It is contemplated that a different number of sensors may be utilized even though for simplicity, mapping device 200 is shown and described as having four sensors 202*a-d* (i.e., two for the horizontal axis and two for the vertical axis). An algorithm is implemented in the processing unit 216 to illuminate appropriate directional indicators 204*a-d* and vary the intensity of the magnetic strength indicator 212. In an embodiment of a suitable algorithm, once one or more directional indicators 204*a-d* are lit, the mapping device 200 should be moved in the direction of the lit directional indicator 204*a-d* until both directional indicators 204*a-d* on the appropriate axis are lit. This procedure is repeated until all of the directional indicators 204*a-d* are lit. Unlike the mapping device 100, the mapping device is less sensitive to distance to the magnet 15 because it utilizes a differential reading from the sensors 202*a-d* as opposed to an absolute value.

The algorithm for mapping device 200 may be described as follows. At start up, reading of the sensors 202*a-d* are taken far from magnet 15 and are averaged to find zero level. When the mapping device 200 approaches magnet 15, the field becomes stronger, and the differential value of two of the sensors 202*a-d*, i.e., a pair of sensors 202*a-d* for each of the horizontal and vertical axes, is calculated. If such differential value exceeds a certain delta value, a directional indicator 204*a-d* is lit up, while the directional indicator 204*a-d* that indicates an opposite value is set to off. If both values are above a certain threshold level, but below delta both lights are set to on. The delta value is dependent on average field strength; it is automatically set to a fraction of the averaged magnetic field measured by all of the sensors 202*a-d*. This is done to compensate field gradient at different distances. At short distances from the magnet 15, the magnetic field detected is much stronger and is less uniform, and the delta is set to a higher value as compared to a situation in which the magnetic field is weak and more uniform, and the difference between the sensor readings is minimal. The algorithm may also implement low-pass digital filters, calibration of the sensors, noise suppression, and a manual recalibration procedure.

Figure 3A:
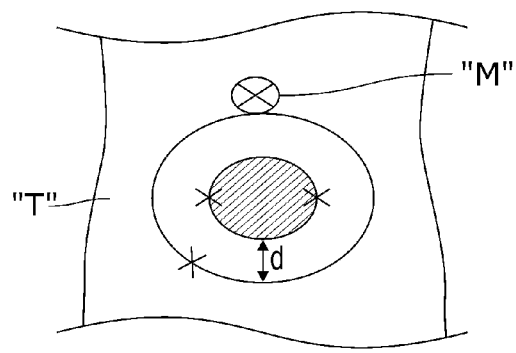
FIG. 3A is a top view of markings on a tissue surface of a patient.
Figure 3B:
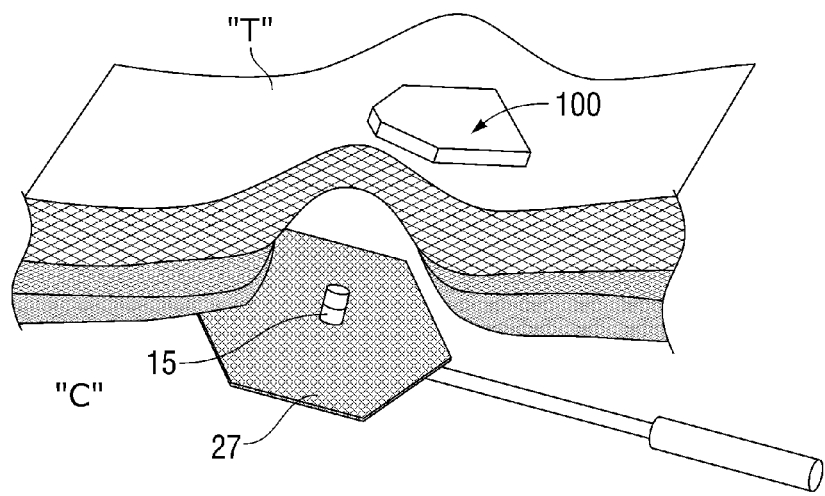
FIG. 3B illustrates deployment of a mesh at the location of the magnet of FIG. 1.

During use, magnets 15 are emplaced at desired locations, e.g., at the locations of hernial defects, and one of the mapping devices 100, 200 is used to detect the location of the magnets under the tissue "S". As shown in FIG. 3A, markings "M" and placed on the surface of the tissue "S", and dimensions d between markings representing the locations or points of interest are calculated. As shown in FIGS. 2 and 3, a marking device 2 is used to place marks on the surface of the tissue "S" at the locations of the magnets 15. In so doing, the surgeon is provided with a landscape map on the surface of the tissue "S". The markings "M" help the surgeon accurately place a device, e.g., a mesh 27, at the locations or points of interest marked by the markings "M".

It will be understood by those skilled in the art that various modifications and changes in form and detail may be made to the present disclosure without departing from the scope and spirit of the same. Therefore, the above description should not be construed as limiting, but merely as exemplifications of particular embodiments. While several embodiments of the disclosure have been shown in the drawings, it is not intended that the disclosure be limited thereto. Rather, the disclosure is intended to be read as broadly in scope as the art will allow.

What is claimed is:

1. A surgical mapping system for locating a structure under tissue comprising:
   at least one magnet that is configured to be implanted under tissue at a location; and a mapping device comprising:
   one or more sensors configured to detect a strength of a magnetic field of the at least one magnet along at least two axes; and
   a processing unit configured to execute the detection of the strength of the magnetic field of the at least one magnet along the at least two axes, wherein the mapping device provides indication when the strength of the magnetic field is substantially equal along the at least two axes to indicate that the mapping device and the at least one magnet are coterminous with respect to the at least two axes, thereby finding the location of the at least one magnet, the mapping device further including a threshold button configured to set a current magnetic field as a baseline magnetic field.

2. The surgical mapping system of claim 1, wherein the mapping device defines an aperture configured to be placed around the location of the at least one magnet with respect to the at least two axes.

3. The surgical mapping system of claim 2, wherein the aperture is configured to receive a marker therethrough to mark the location of the at least one magnet.

4. The surgical mapping system of claim 1, wherein the mapping device further comprises a first surface that is configured to contact and slide across a surface of the tissue.

5. The surgical mapping system of claim 1, wherein a first pair of sensors detect the strength of the magnetic field of the at least one magnet along a horizontal axis, and a second pair of sensors detect the strength of the at least one magnet along a vertical axis along a surface of the tissue.

6. The surgical mapping system of claim 1, wherein guidance to the location of the at least one magnet is provided by calculating a difference between the strength of the magnetic field in a first axis and the strength of the magnetic field in a second axis.

7. The surgical mapping system of claim 1, wherein the mapping system further comprise at least one light source.

8. The surgical mapping system of claim 7, wherein the at least one light source has an intensity corresponding to the strength of the magnetic field detected.

9. The surgical mapping system of claim 7, wherein the at least one light source includes a number of light sources, the number of light sources illuminated corresponds to the strength of the magnetic field detected.

10. The surgical mapping system of claim 1, further including at least one indicator providing directional signals configured to direct movement of the mapping device toward the at least one magnet.

11. The surgical mapping system of claim 1, wherein the one or more sensors has a sensitivity that adjusts in response to a background magnetic field.

12. The surgical mapping system of claim 1, wherein the one or more sensors has a sensitivity that adjusts in response to proximity of the mapping device to the at least one magnet.

13. A method for detecting structures under tissue comprising:
   providing at least one magnet that is configured to be implanted under the tissue at a location;
   implanting the magnet under the tissue at the location;
   providing a surgical mapping device comprising one or more sensors configured to detect a strength of a magnetic field of the at least one magnet along at least two axes and a processing unit configured to execute the detection of the strength of the magnetic field of the at least one magnet along the at least two axes, wherein the mapping device provides indication when the strength of the magnetic field is substantially equal along the at least two axes to indicate that the mapping device and the at least one magnet are coterminous with respect to the at least two axes, thereby finding the location of the at least one magnet, the mapping device further including a threshold button configured to set a current magnetic field as a baseline magnetic field;
   moving the surgical mapping device along the at least two axes with respect to the tissue; and
   locating the at least one magnet by observing indication from the surgical mapping device.

14. The method of claim 13 further comprising marking the location of the at least one magnet.

* * * * *